US012565670B2

(12) United States Patent
Lee et al.

(10) Patent No.: US 12,565,670 B2
(45) Date of Patent: Mar. 3, 2026

(54) **MICROORGANISM OF THE GENUS *CORYNEBACTERIUM* FOR PRODUCING L-AMINO ACID AND METHOD FOR PRODUCING L-AMINO ACID USING THE SAME**

(71) Applicant: CJ CHEILJEDANG CORPORATION, Seoul (KR)

(72) Inventors: Han Hyoung Lee, Seoul (KR); Hyo Jeong Byun, Seoul (KR); Byeong Soo Kim, Seoul (KR); Hee Ju Kim, Seoul (KR); Moo Young Jung, Seoul (KR); Hyung Joon Kim, Seoul (KR); Seul-Gi Park, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 354 days.

(21) Appl. No.: 18/464,158

(22) Filed: Sep. 8, 2023

(65) Prior Publication Data

US 2024/0043886 A1 Feb. 8, 2024

Related U.S. Application Data

(63) Continuation-in-part of application No. PCT/KR2022/002505, filed on Feb. 21, 2022.

(30) Foreign Application Priority Data

Mar. 8, 2021 (KR) ........................ 10-2021-0030087

(51) Int. Cl.
| | |
|---|---|
| *C12P 13/22* | (2006.01) |
| *C12N 9/04* | (2006.01) |
| *C12N 9/12* | (2006.01) |
| *C12P 13/08* | (2006.01) |

(52) U.S. Cl.
CPC .......... *C12P 13/227* (2013.01); *C12N 9/0006* (2013.01); *C12N 9/1205* (2013.01); *C12P 13/08* (2013.01); *C12Y 101/01049* (2013.01); *C12Y 207/01004* (2013.01)

(58) Field of Classification Search
CPC .. C12Y 207/01004; C12P 13/22; C12P 13/08; C12N 9/0004; C12N 15/67
See application file for complete search history.

(56) References Cited

U.S. PATENT DOCUMENTS

| | | | |
|---|---|---|---|
| 7,662,943 B2 | 2/2010 | Park et al. | |
| 8,932,861 B2 | 1/2015 | Jang et al. | |
| 10,584,338 B2 | 3/2020 | Lee et al. | |
| 2012/0142064 A1 | 6/2012 | Van Dyk | |

FOREIGN PATENT DOCUMENTS

| | | | |
|---|---|---|---|
| EP | 1302537 A1 | 4/2003 |
| JP | 2014-510535 A | 5/2014 |
| KR | 10-0159812 B1 | 8/1998 |
| KR | 10-0924065 B1 | 10/2009 |
| KR | 10-2012-0111807 A | 10/2012 |
| KR | 10-1208480 B1 | 11/2012 |
| KR | 10-2035844 B1 | 10/2019 |
| WO | 01/98472 A1 | 12/2001 |
| WO | 2006/138689 A2 | 12/2006 |
| WO | 2012/134253 A2 | 10/2012 |

OTHER PUBLICATIONS

Office Action issued in corresponding Japanese Patent Application No. 2023-546556 dated Jun. 25, 2024.
Becker et al., "Metabolic flux engineering of l-lysine production in Corynebacterium glutamicum—over expression and modification of G6P dehydrogenase," Journal of Biotechnology, 132: 99-109 (2007).
NCBI, GenBank accession No. BAB98969.1 Glucose-6-phosphate 1-dehydrogenase [Corynebacterium glutamicum ATCC 13032] Oct. 7, 2016.
NCBI, GenBank accession No. WP_038584208.1 glucose-6-phosphate dehydrogenase [Corynebacterium glutamicum] Jun. 19, 2019.
NCBI, GenBank accession No. WP_001274885.1 aminoimidazole riboside kinase [*Escherichia coli*] Nov. 28, 2019.
Binder et al. "A high-throughput approach to identify genomic variants of bacterial metabolite producers at the single-cell level," Genome Biology, 13: R40 (2012).
Gibson et al., "Enzymatic assembly of DNA molecules up to several hundred kilobases," Nature Methods, 6 (5): 343-347 (May 2009).
Van der Rest et al., "A heat shock following electroporation induces highly efficient transformation of Corynebacterium glutamicum with xenogeneic plasmid DNA," Appl. Microbiol.Biotechnol. 52: 541-545 (1999).
Kjeldsen at el., "In Silico Genome-Scale Reconstruction and Validation of the Corynebacterium glutamicum Metabolic Network," Biotechnology and Bioengineering, 102 (2): 583-597 (2009).
International Search Report issued in corresponding International Patent Application No. PCT/KR2022/002505 dated Jun. 13, 2022.
Extended European Search Report dated Jun. 25, 2024, issued in European Patent Application No. 22767363.9.

*Primary Examiner* — Tekchand Saidha

(74) *Attorney, Agent, or Firm* — Morgan, Lewis & Bockius LLP

(57) ABSTRACT

The present disclosure relates to a microorganism of the genus *Corynebacterium* producing L-amino acid, a method for producing L-amino acid using the same, use of L-amino acid production, and a composition for producing L-amino acid.

11 Claims, No Drawings
Specification includes a Sequence Listing.

MICROORGANISM OF THE GENUS *CORYNEBACTERIUM* FOR PRODUCING L-AMINO ACID AND METHOD FOR PRODUCING L-AMINO ACID USING THE SAME

A computer readable text file, entitled "SequenceListing.txt," created on or about Sep. 8, 2023, with a file size of 66,580 bytes contains the sequence listing for this application and is hereby incorporated by reference in its entirety.

TECHNICAL FIELD

The present disclosure relates to a microorganism of the genus *Corynebacterium* producing L-amino acid, a method for producing L-amino acid using the same, use of L-amino acid production, and a composition for producing L-amino acid.

BACKGROUND ART

L-Amino acids are basic structural units of proteins, and are used as important materials for pharmaceuticals, food additives, animal feeds, nutrients, pesticides, bactericides, etc. Among L-amino acids, L-lysine is an essential amino acid that is not biosynthesized in the living body and is known to be necessary for growth promotion, calcium metabolism, promotion of gastric juice secretion, and resistance to diseases. L-Lysine is variously used in feeds, medical products, foods, etc. Additionally, L-tryptophan is also one of the essential amino acids and is used for feed additives, infusions, pharmaceuticals and health food materials, etc.

Meanwhile, strains of the genus *Corynebacterium*, especially *Corynebacterium glutamicum*, are gram-positive microorganisms widely used in producing L-amino acids and other useful substances. Many studies have been conducted to develop a microorganism with high production efficiency and a fermentation technology for producing the amino acids. For example, target material-specific approaches to increase expression of a gene encoding an enzyme involved in amino acid biosynthesis or to remove unnecessary genes in amino acid biosynthesis in a strain of the genus *Corynebacterium* are mainly used (Korean Patent Nos. 10-0924065 and 10-1208480). In addition to these methods, a method of deleting genes which are not involved in the amino acid production and a method of deleting genes of which specific functions in the amino acid production are not known are also used. However, there is still a demand for research on a method capable of efficiently producing L-amino acids with a high yield.

DISCLOSURE

Technical Problem

The problem to be solved of the present disclosure is to provide a microorganism of the genus *Corynebacterium*, in which the activity of glucose-6-phosphate 1-dehydrogenase and fructokinase is enhanced.

Technical Solution

One object of the present disclosure is to provide a microorganism of the genus *Corynebacterium* producing L-amino acid, in which the activity of glucose-6-phosphate 1-dehydrogenase and fructokinase is enhanced.

Another object of the present disclosure is to provide a method for producing L-amino acid using the microorganism.

Still another object of the present disclosure is to provide the use of L-amino acid production of the microorganism.

Yet another object of the present disclosure is to provide a composition for producing L-amino acid, including the microorganism; and/or a culture of the microorganism.

Advantageous Effects

The microorganism of the genus *Corynebacterium*, in which the activity of glucose-6-phosphate 1-dehydrogenase and fructokinase is enhanced, can produce L-amino acid with high efficiency.

DETAILED DESCRIPTION OF PREFERRED EMBODIMENTS

The present disclosure will be described in detail as follows. Meanwhile, each description and embodiment disclosed herein can be applied to other descriptions and embodiments, respectively. That is, all combinations of various elements disclosed herein fall within the scope of the present disclosure. Further, the scope of the present disclosure is not limited by the specific description described below. Additionally, a number of papers and patent documents have been cited throughout the present specification. The contents of the cited papers and patent documents are incorporated herein by reference in their entirety, and the level of the technical field to which the present disclosure belongs and the contents of the present disclosure will be described more clearly.

One aspect of the present disclosure provides a microorganism of the genus *Corynebacterium* producing L-amino acid, in which the activity of glucose-6-phosphate 1-dehydrogenase and fructokinase is enhanced.

As used herein, the term "L-amino acid" may include all L-amino acids which may be produced by a microorganism from many different kinds of carbon sources through metabolic processes. Specifically, the L-amino acid may include basic amino acids such as L-lysine, L-arginine, L-histidine, etc., non-polar amino acids such as L-valine, L-leucine, L-glycine, L, isoleucine, L-alanine, L-proline, L-methionine, etc., polar amino acids such as L-serine, L-threonine, L-cysteine, L-asparagine, L-glutamine, etc., aromatic amino acids such as L-phenylalanine, L-tyrosine, L-tryptophan, etc., and acidic amino acids such as L-glutamic acid, L-aspartic acid, etc. More specifically, the L-amino acid herein may be L-lysine or L-tryptophan, but is not limited thereto.

As used herein, the term "glucose-6-phosphate 1-dehydrogenase" (hereinafter referred to as "Zwf") is involved in the pentose phosphate pathway, which is a metabolic pathway, and plays a role in reducing $NADP^+$ to NADPH, oxidizing glucose-6-phosphate.

For the purpose of the present disclosure, the protein may also be named "G6PD", "G6PDH", "glucose-6-phosphate dehydrogenase", or "Zwf". The gene encoding the protein may be, for example, the zwf gene, but is not limited thereto. In the present disclosure, the "zwf gene" may be used interchangeably with the "gene encoding glucose-6-phosphate 1-dehydrogenase". Additionally, the protein may be, for example, the same protein as the protein derived from *Corynebacterium glutamicum*, but is not limited thereto as long as it can increase the production of L-amino acid.

The Zwf may have or consist of an amino acid sequence of SEQ ID NO: 1 or SEQ ID NO: 3, or may include an amino acid sequence represented by SEQ ID NO: 1 or SEQ ID NO: 3, but is not limited thereto. The sequences of SEQ ID NO: 1 or SEQ ID NO: 3 may be confirmed from NCBI GenBank, a known database.

The Zwf may include a nucleotide sequence encoding an amino acid sequence represented by SEQ ID NO: 2 or SEQ ID NO: 4, but is not limited thereto. The sequences of SEQ ID NO: 2 or SEQ ID NO: 4 can be confirmed from NCBI GenBank, a known database.

Specifically, the Zwf may be an amino acid sequence of SEQ ID NO: 1 or SEQ ID NO: 3 and/or an amino acid sequence having a homology or identity of at least 70%, 80%, 85%, 90%, 95%, 96%, 97%, 98%, or 99% or more with SEQ ID NO: 1 or SEQ ID NO: 3. Additionally, it is apparent that Zwf having an amino acid sequence, in which a part of the amino acid sequence is deleted, modified, substituted, or added, may fall within the scope of the present disclosure, as long as the amino acid sequence has such homology or identity and shows a function corresponding to Zwf.

As used herein, the term "fructokinase" (hereinafter referred to as "CscK") refers to an enzyme catalyzing a reaction for producing D-fructose-6-phosphate and ADP by transferring phosphate in the presence of ATP.

For the purpose of the present disclosure, the protein may also be named "fructose kinase", "fructokinase", or "CscK". The gene encoding the protein may be, for example, the csck gene, but is not limited thereto. In the present disclosure, the "csck gene" may be used interchangeably with the "gene encoding fructokinase". Additionally, the protein may be, for example, the same protein as the protein derived from *Escherichia coli*, but is not limited thereto as long as it can increase the production of L-amino acids.

The CscK may have or consist of an amino acid sequence of SEQ ID NO: 5, or may include an amino acid sequence represented by SEQ ID NO: 5, but is not limited thereto. The sequence of SEQ ID NO: 5 can be confirmed from NCBI GenBank, a known database.

The CscK may include a nucleotide sequence encoding an amino acid sequence represented by SEQ ID NO: 6, but is not limited thereto. The sequence of SEQ ID NO: 6 can be confirmed from NCBI GenBank, a known database.

Specifically, the CscK may be an amino acid sequence of SEQ ID NO: 5 and/or an amino acid sequence having a homology or identity of at least 70%, 80%, 85%, 90%, 95%, 96%, 97%, 98%, or 99% or more with SEQ ID NO: 5. Additionally, it is apparent that CscK having an amino acid sequence, in which a part of the amino acid sequence is deleted, modified, substituted, or added, may fall within the scope of the present disclosure, as long as the amino acid sequence has such homology or identity and shows a function corresponding to CscK.

As used herein, the term "homology" or "identity" refers to a degree of relevance between two given amino acid sequences or nucleotide sequences, and may be expressed as a percentage. The terms homology and identity may often be used interchangeably with each other.

The sequence homology or identity of conserved polynucleotides or polypeptides may be determined by standard alignment algorithms and can be used with a default gap penalty established by the program being used. Substantially, homologous or identical sequences are generally expected to hybridize to all or at least about 50%, 60%, 70%, 80%, or 90% of the entire length of the sequences under moderate or high stringent conditions. Polynucleotides that contain degenerate codons instead of codons in hybridizing polynucleotides are also considered.

The homology or identity of the polypeptide or polynucleotide sequences may be determined by, for example, BLAST algorithm by literature (see Karlin and Altschul, Pro. *Natl. Acad. Sci. USA*, 90, 5873 (1993)), or FASTA by Pearson (see: Methods Enzymol., 183, 63, 1990). Based on the algorithm BLAST, a program referred to as BLASTN or BLASTX has been developed (see http://www.ncbi.nlm.nih-.gov). Further, whether any amino acid or polynucleotide sequences have a homology, similarity, or identity with each other, it may be identified by comparing the sequences in a Southern hybridization experiment under stringent conditions as defined, and appropriate hybridization conditions defined are within the skill of the art, and may be determined by a method well known to those skilled in the art (for example, J. Sambrook et al., *Molecular Cloning, A Laboratory Manual,* 2nd Edition, Cold Spring Harbor Laboratory press, Cold Spring Harbor, New York, 1989; F. M. Ausubel et al., *Current Protocols in Molecular Biology*).

Specifically, the "microorganism producing L-amino acid" includes all wild-type microorganisms, or naturally or artificially genetically modified microorganisms. Specifically, it may be a microorganism in which a particular mechanism is weakened or enhanced due to insertion of a foreign gene, or enhancement or inactivation of the activity of an endogenous gene, and it may be a microorganism in which genetic mutation occurs or L-amino acid-producing activity is enhanced for the production of the desired L-amino acid. For the purpose of the present disclosure, the microorganism producing L-amino acid has a feature in that the ability to produce the desired L-amino acid is increased by enhancing the expression or activity of the Zwf and Csck proteins, and may be a genetically modified microorganism or a recombinant microorganism, but is not limited thereto.

As used herein, the term "enhancement of activity" of a protein means that the activity of a protein is increased compared to its endogenous activity. The "endogenous activity" refers to the activity of a particular protein originally possessed by a parent strain before transformation or a non-modified microorganism, when a trait is altered through genetic modification caused by natural or artificial factors, and may be used interchangeably with "activity before modification". The "increase" in the activity of a protein compared to its endogenous activity means that the activity of the protein is enhanced compared to that of a particular protein originally possessed by a parent strain before transformation or a non-modified microorganism.

The "enhancement of activity" may be achieved by introducing a foreign protein, or by enhancing the activity of the endogenous protein, and may specifically be achieved by enhancing the activity of the endogenous protein. The enhancement of the activity of the protein can be confirmed by the increase in the level of activity of the protein, expression level, or the amount of product produced from the protein.

The enhancement of the activity can be applied by various methods well known in the art, and is not limited as long as it can enhance the activity of the target protein compared to that of the microorganism before modification. Specifically, genetic engineering and/or protein engineering well known to those skilled in the art, which is a common method of molecular biology, may be used, but the method is not limited thereto (e.g., Sitnicka et al. Functional Analysis of Genes. *Advances in Cell Biology.* 2010, Vol. 2. 1-16; Sambrook et al. *Molecular Cloning* 2012; etc.).

In the present disclosure, the protein target for the activity enhancement, that is, the target protein may be Zwf and Csck, but is not limited thereto.

Specifically, the enhancement of the activity of the protein of the present disclosure may be achieved by:

1) increasing the intracellular copy number of a gene encoding the protein;

2) replacing the expression regulatory sequence of a gene encoding the protein on the chromosome with a sequence having a strong activity;

3) modifying the nucleotide sequence encoding the initiation codon or 5'-UTR of the gene transcript encoding the protein;

4) modifying the amino acid sequence such that the activity of the protein is enhanced;

5) modifying the polynucleotide sequence encoding the protein such that the activity of the protein is enhanced (e.g., modifying the gene sequence encoding the protein to encode a protein that has been modified to enhance the activity);

6) introducing a foreign polynucleotide exhibiting the activity of the protein or a codon-optimized variant polynucleotide of the polynucleotide;

7) codon optimization of the polynucleotide encoding the protein;

8) analyzing the tertiary structure of the protein and thereby selecting and modifying the exposed site, or chemically modifying the same; or 9) a combination of two or more selected from above 1 to 8), but is not limited thereto.

Specifically, the 1) method of increasing the intracellular copy number of a gene encoding the protein may be achieved by way of any method known in the art, for example, by introducing a vector, which is operably linked to the gene encoding the protein and is able to replicate and function regardless of a host cell, into the host cell. The method may be performed by introducing a vector, which is operably linked to the gene and is able to insert the gene into the chromosome of a host cell, into the host cell, but is not limited thereto.

As used herein, the term "vector" refers to a DNA construct containing the polynucleotide sequence encoding the target protein operably linked to a suitable regulatory sequence so as to be able to express the target protein in a suitable host cell. The expression regulatory sequence may include a promoter capable of initiating transcription, any operator sequence for regulating the transcription, a sequence encoding a suitable mRNA ribosome-binding site, and a sequence for regulating termination of transcription and translation. Once transformed into a suitable host cell, the vector may replicate or function independently from the host genome, or may integrate into genome thereof.

The vector used in the present disclosure is not particularly limited, and any vector known in the art may be used. Examples of the vector typically used may include natural or recombinant plasmids, cosmids, viruses, and bacteriophages. For example, as a phage vector or cosmid vector, pWE15, M13, MBL3, MBL4, IXII, ASHII, APII, t10, t11, Charon4A, and Charon21A, etc. may be used; and as a plasmid vector, those based on pDZ, pBR, pUC, pBluescriptII, pGEM, pTZ, pCL, pET, etc. may be used. Specifically, pDZ, pDC, pDCM2, pACYC177, pACYC184, pCL, pECCG117, pUC19, pBR322, pMW118, pCC1 BAC vectors, etc. may be used.

As used herein, the term "transformation" refers to the introduction of a recombinant vector containing a polynucleotide encoding a target protein into a host cell so that the protein encoded by the polynucleotide can be expressed in the host cell. As long as the transformed polynucleotide can be expressed in the host cell, it does not matter whether the transformed polynucleotide is integrated into the chromosome of the host cell and located therein or located extra-chromosomally, and both cases can be included. The method for transforming the vector includes any method of introducing a nucleic acid into a cell, and may be performed by selecting a suitable standard technique as known in the art depending on the host cell. For example, the transformation may be carried out via electroporation, calcium phosphate (CaPO₄) precipitation, calcium chloride (CaCl₂)) precipitation, microinjection, a polyethylene glycol (PEG) technique, a DEAE-dextran technique, a cationic liposome technique, a lithium acetate-DMSO technique, etc., but the method is not limited thereto.

Further, as used herein, the term "operably linked" means that the polynucleotide sequence is functionally linked to a promoter sequence or expression regulatory region that initiates and mediates transcription of the polynucleotide encoding the target protein of the present disclosure. The operable linkage may be prepared using a genetic recombinant technology well known in the art, and site-specific DNA cleavage and linkage may be prepared using cleavage and linking enzymes, etc. known in the art, but is not limited thereto.

The 2) method of replacing the expression regulatory sequence of a gene encoding the protein on the chromosome with a sequence having a strong activity may be achieved by way of any method known in the art, for example, by inducing a modification on the sequence through deletion, insertion, non-conservative or conservative substitution of the nucleic acid sequence, or a combination thereof to further enhance the activity of the expression regulatory sequence or by replacing the sequence with a nucleic acid sequence having a stronger activity. The expression regulatory sequence may include, but is not particularly limited to, a promoter, an operator sequence, a sequence encoding a ribosome binding site, a sequence regulating the termination of transcription and translation, etc. The method may specifically include linking a strong heterologous promoter instead of the original promoter, but is not limited thereto.

Examples of the strong promoter may include CJ1 to CJ7 promoters (U.S. Pat. No. 7,662,943 B2), lac promoter, trp promoter, trc promoter, tac promoter, lambda phage PR promoter, PL promoter, tet promoter, and rmf promoter, etc., but are not limited thereto, and may include all substitutions with a stronger promoter compared to its endogenous activity.

The 3) method of modifying the nucleotide sequence of the initiation codon or 5'-UTR of the gene transcript encoding the protein may be achieved by way of any method known in the art, for example, by substituting the endogenous initiation codon of the protein with another initiation codon having a higher expression rate of the protein compared to the endogenous initiation codon, but is not limited thereto.

The 4) and 5) methods of modifying the amino acid sequence or the polynucleotide sequence may be achieved by way of any method known in the art, for example, by inducing a modification on the sequence through deletion, insertion, non-conservative or conservative substitution of the polynucleotide sequence or a combination thereof to further enhance the activity of the polynucleotide sequence, or by replacing the sequence with a polynucleotide sequence modified to have a stronger activity. The replacement may specifically be performed by inserting the gene into the chromosome by homologous recombination, but is not limited thereto. The vector used herein may further include a selection marker to confirm the insertion into the chromosome. The selection marker is for selecting the cells transformed with the vector, that is, for confirming the insertion of the gene to be introduced, and markers that provide selectable phenotypes, such as drug resistance, auxotrophy, resistance to cell toxic agents, or expression of surface proteins, may be used. Only cells expressing the selection marker are able to survive or to show different phenotypes under the environment treated with the selective agent, and thus the transformed cells may be selected.

The 6) method of introducing a foreign polynucleotide having the activity of the protein may be achieved by way of any method known in the art, for example, by introducing into a host cell a foreign polynucleotide encoding a protein that exhibits the same or similar activity to the protein or a codon-optimized variant polynucleotide thereof. The foreign polynucleotide may be used without limitation regardless of its origin or sequence as long as it exhibits the same or similar activity to the protein. In addition, the introduced foreign polynucleotide may be introduced into the host cell by optimizing its codons so that the optimized transcription and translation are achieved in the host cell. The introduction may be performed by those of ordinary skill in the art by appropriately selecting a transformation method known in the art, and the expression of the introduced polynucleotide in the host cell enables to produce the protein, thereby increasing its activity.

The 7) method of codon optimization of the polynucleotide encoding the protein may be achieved by codon optimization of an endogenous polynucleotide to increase the transcription or translation within a host cell, or by optimizing its codons such that the optimized transcription and translation of the foreign polynucleotide can be achieved within the host cell.

The 8) method of analyzing the tertiary structure of the protein and thereby selecting and modifying the exposed site, or chemically modifying the same, may be achieved, for example, by comparing the sequence information of the polypeptide to be analyzed with a database, in which the sequence information of known proteins is stored, to determine template protein candidates according to the degree of sequence similarity, and thus confirming the structure based on the information to thereby select and transform or modify the exposed site to be modified or chemically modified.

Such enhancement of the protein activity may mean that the activity or concentration of the corresponding protein is increased relative to the activity or concentration of the protein expressed in a wild-type or a microorganism before modification, or that the amount of product produced from the protein is increased, but is not limited thereto. As used herein, the term "strain before modification" or "microorganism before modification" does not exclude a strain containing a mutation that may occur naturally in a microorganism, and may refer to a natural-type strain itself, or a strain before the trait is altered due to genetic modification caused by natural or artificial factors. In the present disclosure, the modification of the traits may be an enhancement of the Zwf and CscK activity. The "strain before modification" or "microorganism before modification" may be used interchangeably with "non-mutant strain", "non-modified strain", "non-mutant microorganism", "non-modified microorganism", or "reference microorganism".

In the present disclosure, the reference microorganism is not particularly limited as long as it is a microorganism that produces L-amino acid, and mutant strains with an enhanced L-amino acid producing ability compared to the wild-type are also included without limitation. Examples thereof include strains in which one or more genetic modifications are added to the strains of L-lysine-producing *Corynebacterium glutamicum* KCCM11016P (Korean Patent No. 10-0159812), KCCM10770P (Korean Patent No. 10-0924065), and CJ3P (Binder et al. *Genome Biology* 2012, 13:R40), or L-tryptophan-producing *Corynebacterium glutamicum* KCCM12218P (Korean Patent No. 10-2035844), in order to enhance the biosynthesis pathways of the strains, but are not limited thereto.

For the purpose of the present disclosure, the microorganism producing L-amino acid may be any microorganism, as long as it is a microorganism capable of producing L-amino acid, in which the activity of Zwf and Csck are enhanced by the above-described method. As used herein, the "microorganism producing L-amino acid" may be used interchangeably with "L-amino acid-producing microorganism", or "microorganism having an L-amino acid producing ability", and specifically a microorganism of the genus *Corynebacterium*, but is not limited thereto.

As used herein, the "microorganism of the genus *Corynebacterium*" may include all microorganisms of the genus *Corynebacterium*. Specifically, it may be *Corynebacterium glutamicum, Corynebacterium crudilactis, Corynebacterium deserti, Corynebacterium efficiens, Corynebacterium callunae, Corynebacterium stationis, Corynebacterium singulare, Corynebacterium halotolerans, Corynebacterium striatum, Corynebacterium ammoniagenes, Corynebacterium pollutisoli, Corynebacterium imitans, Corynebacterium testudinoris,* or *Corynebacterium flavescens,* and more specifically *Corynebacterium glutamicum.*

Meanwhile, it has already been known that the microorganisms of the genus *Corynebacterium* can produce L-amino acid; however, the productivity thereof is too low, and genes or mechanisms involved in the production of L-amino acid have not yet all been revealed. Accordingly, the "microorganism of the genus *Corynebacterium* producing L-amino acid" may be a natural wild-type microorganism itself, a microorganism of the genus *Corynebacterium* having an enhanced L-amino acid producing ability by enhancing or inactivating the activity of genes involved in L-amino acid production mechanism, or a microorganism of the genus *Corynebacterium* having an enhanced L-amino acid producing ability by introducing or enhancing the activity of a foreign gene.

Another aspect of the present disclosure provides a method for producing L-amino acid, including: culturing the microorganism according to the present disclosure in a medium; and recovering the L-amino acid from the microorganism or medium.

The microorganism according to the present disclosure is the same as described above.

In the method of the present disclosure, the culturing of the microorganism of the genus *Corynebacterium* may be carried out using any culturing conditions and methods known in the art.

As used herein, the term "culturing" means that a microorganism is allowed to grow under suitably and artificially controlled environmental conditions. In the present disclosure, the method of producing L-amino acid using the microorganism for producing L-amino acid may be carried out using a method widely known in the art. Specifically, the culturing may be carried out by a batch process, a fed batch or repeated fed batch process in a continuous manner, but is not limited thereto. The medium used for culturing should meet the requirements of the particular strain in an appropriate way. The culture medium for the *Corynebacterium* strains is known in the art (e.g., *Manual of Methods for*

*General Bacteriology by the American Society for Bacteriology*, Washington D.C., USA, 1981).

Carbon sources that can be used in the medium may include sugars and carbohydrates such as glucose, saccharose, lactose, fructose, maltose, starch, and cellulose; oils and fats such as soybean oil, sunflower oil, castor oil, and coconut oil; fatty acids such as palmitic acid, stearic acid, and linoleic acid; alcohols such as glycerol and ethanol; and organic acids such as acetic acid. These substances may be used alone or in a mixture, but are not limited thereto.

Nitrogen sources that can be used may include peptone, a yeast extract, a meat extract, a malt extract, corn steep liquor, soybean cake, and urea or inorganic compounds, such as ammonium sulfate, ammonium chloride, ammonium phosphate, ammonium carbonate, and ammonium nitrate. These nitrogen sources may also be used alone or in a mixture, but are not limited thereto.

Phosphorus sources that can be included in the medium may include potassium dihydrogen phosphate or dipotassium hydrogen phosphate, or corresponding sodium-containing salts. In addition, the culture medium may include a metal salt such as magnesium sulfate or iron sulfate, which is required for the growth. Further, in addition to the above-described substances, essential growth substances such as amino acids and vitamins may be used. Additionally, precursors suitable for the culture medium may be used. These substances may be appropriately added to the culture during culturing in a batch or continuous manner, but are not limited thereto.

Basic compounds such as sodium hydroxide, potassium hydroxide, or ammonia, or acidic compounds such as phosphoric acid or sulfuric acid may be added during culturing of the microorganism in a suitable manner to thereby adjust the pH of the culture. In addition, an anti-foaming agent such as fatty acid polyglycol ester may be used to suppress the formation of bubbles. In order to maintain aerobic conditions, oxygen or oxygen-containing gas (e.g., air) may be injected into the culture. The temperature of the culture may be usually 20° C. to 45° C., specifically 25° C. to 40° C. The culturing may be continued until a desired amount of L-amino acid is produced, and it may specifically be achieved within 10 hours to 160 hours, but is not limited thereto.

The present disclosure may additionally include a step of preparing a medium before the culturing step in the method of the present disclosure, but is not limited thereto.

L-amino acid may be separated from the culture by way of a common method known in the art. The separation methods may include centrifugation, filtration, chromatography, crystallization, etc. For example, a supernatant, obtained by centrifuging the culture at a low speed and removing biomass, may be separated by ion exchange chromatography, but is not limited thereto.

Further, the step of recovering may further include a purification process, and the purification process may be performed by way of a suitable method known in the art.

Still another aspect of the present disclosure provides the use of L-amino acid production of the microorganism of the present disclosure.

The microorganism and L-amino acid according to the present disclosure are the same as described above.

Yet another aspect of the present disclosure provides a composition for producing L-amino acid, including: the microorganism according to the present disclosure; and/or a culture of the microorganism.

The microorganism and L-amino acid according to the present disclosure are as described above.

MODE FOR CARRYING OUT THE INVENTION

Hereinafter, the present disclosure will be described in detail by way of Examples. However, these Examples are given for illustrative purposes only, and the scope of the invention is not intended to be limited to or by these Examples.

Example 1. Construction of Enhanced Vectors

Example 1-1. Construction of Vectors in which *Corynebacterium glutamicum* ATCC13032-Derived Glucose-6-Phosphate 1-Dehydrogenase Gene (zwt) is Enhanced The effect of enhancing the gene was confirmed by introducing zwf in which each of the SPL13 promoter (U.S. Ser. No. 10/584,338 B2) and the CJ7 promoter (U.S. Pat. No. 7,662,943 B2) is connected into the transposon of *Corynebacterium glutamicum* ATCC13032.

The zwf was used for the *Corynebacterium glutamicum* ATCC13032 genomic DNA as a template. Further, primers containing the polynucleotides of SEQ ID NOS: 9 and 10 (Table 1) and SEQ ID NOS: 13 and 14 (Table 2) were prepared based on the NCBI nucleotide sequence (NC_003450.3) information, and PCR (Solg™ Pfu-X DNA polymerase) was performed under the conditions of Table 4 to thereby obtain zwf gene fragments for preparing vectors.

TABLE 1

Primer Sequences of pDZTn-Pspl13-zwf(C.gl13032)

| No. | Name | DNA Sequences |
|---|---|---|
| SEQ ID NO: 7 | primer 1 | GCAGAAGGAATGAGTTCCTCGGCGCTTC ATGTCAACAATC |
| SEQ ID NO: 8 | primer 2 | tgttttgatctcctccaataatc |
| SEQ ID NO: 9 | primer 3 | tattggaggagatcaaaacaGTGAGCAC AAACACG |
| SEQ ID NO: 10 | primer 4 | GTTATTAGATGTCGGGCCCATTATGGCC TGCGCCAGGTGT |

TABLE 2

Primer Sequences of pDZTn-Pcj7-zwf(C.gl13032)

| No. | Name | DNA Sequences |
|---|---|---|
| SEQ ID NO: 11 | primer 5 | GCAGAAGGAATGAGTTCCTCagaaacat cccagcgctact |
| SEQ ID NO: 12 | primer 6 | gagtgtttcctttcgttgggtac |
| SEQ ID NO: 13 | primer 7 | cccaacgaaaggaaacactcGTGAGCAC AAACACG |
| SEQ ID NO: 14 | primer 8 | GTTATTAGATGTCGGGCCCATTATGGCC TGCGCCAGGTGT |

TABLE 3

Primer Sequences for Confirming Construction
of Vectors and Strains

| No. | Name | DNA Sequences |
|---|---|---|
| SEQ ID NO: 47 | primer 41 | ACGACGCTGGTATTTCTCCC |
| SEQ ID NO: 48 | primer 42 | TGATTGTCGATATGACCGGG |

TABLE 4

PCR Conditions

| Step | Temperature | Time |
|---|---|---|
| Initialization | 95° C. | 10 minutes |
| Denaturation | 95° C. | 30 seconds |
| Annealing | 62° C. | 30 seconds |
| Elongation | 72° C. | 1-2 minutes |
| Post Elongation | 72° C. | 5 minutes |

In order to obtain the SPL13 promoter and the CJ7 promoter derived from *Corynebacterium ammoniagenes*, PCR (Solg™ Pfu-X DNA polymerase) was performed (Table 4) using the primers of SEQ ID NOS: 7 and 8 (Table 1) and SEQ ID NOS: 11 and 12 (Table 2).

The amplified SPL13, CJ7 promoter regions, zwf gene fragments, and pDZTn vector (U.S. Pat. No. 8,932,861 B2) cleaved with ScaI restriction enzyme were linked by way of the Gibson assembly method (D. G. Gibson et al., *NATURE METHODS*, Vol. 6 No. 5, MAY 2009, NEBuilder HiFi DNA Assembly Master Mix), and then transformed into *E. coli* DH5a and plated on an LB solid medium containing kanamycin (25 mg/L). In order to select colonies transformed with the vector in which the desired gene and pDZTn were linked, PCR was performed using the primers of SEQ ID NOS: 47 and 48 (Table 3). Plasmids were obtained from the selected colonies using a commonly known plasmid extraction method, and the resulting plasmids were named pDZTn-Pspl13-zwf(C.gl13032) and pDZTn-Pcj7-zwf (C.gl13032).

Example 1-2. Construction of Vectors in which *Corynebacterium glutamicum* ATCC13869-Derived Glucose-6-Phosphate 1-Dehydrogenase Gene (zwt) is Enhanced The effect of enhancing the *Corynebacterium glutamicum* ATCC13869-derived zwf gene was confirmed using the *Corynebacterium glutamicum* ATCC13869 genomic DNA as a template. Further, primers containing the polynucleotides of SEQ ID NOS: 17 and 18 (Table 5) and SEQ ID NOS: 21 and 22 (Table 6) were prepared based on the information about the *Corynebacterium glutamicum* ATCC13869 gene and surrounding nucleotide sequences registered with the National Institutes of Health (NIH GenBank) and PCR (Solg™ Pfu-X DNA polymerase) was performed under the conditions of Table 4 to thereby obtain zwf gene fragments for preparing vectors.

TABLE 5

Primer Sequences of pDZTn-Pspl13-zwf(C.gl13869)

| No. | Name | DNA Sequences |
|---|---|---|
| SEQ ID NO: 15 | primer 9 | GCAGAAGGAATGAGTTCCTCGGC GCTTCATGTCAACAATC |

TABLE 5-continued

Primer Sequences of pDZTn-Pspl13-zwf(C.gl13869)

| No. | Name | DNA Sequences |
|---|---|---|
| SEQ ID NO: 16 | primer 10 | tgttttgatctcctccaataatc |
| SEQ ID NO: 17 | primer 11 | tattggaggagatcaaaacaGTG AGCACAAACACG |
| SEQ ID NO: 18 | primer 12 | GTTATTAGATGTCGGGCCCATTA TGGCCTGCGCCAGGTGT |

TABLE 6

Primer Sequences of pDZTn-Pcj7-zwf(C.gl13869)

| No. | Name | DNA Sequences |
|---|---|---|
| SEQ ID NO: 19 | primer 13 | GCAGAAGGAATGAGTTCCTCagaa acatcccagcgctact |
| SEQ ID NO: 20 | primer 14 | gagtgtttcctttcgttgggtac |
| SEQ ID NO: 21 | primer 15 | cccaacgaaaggaaacactcGTGA GCACAAACACG |
| SEQ ID NO: 22 | primer 16 | GTTATTAGATGTCGGGCCCATTAT GGCCTGCGCCAGGTGT |

In order to obtain the SPL13 promoter and the CJ7 promoter derived from *Corynebacterium ammoniagenes*, PCR (Solg™ Pfu-X DNA polymerase) was performed using the primers of SEQ ID NOS: 15 and 16 (Table 5) and SEQ ID NOS: 19 and 20 (Table 6) under the conditions of Table 4.

The amplified SPL13, CJ7 promoter regions, zwf gene fragments, and pDZTn vector (U.S. Pat. No. 8,932,861 B2) cleaved with ScaI restriction enzyme were linked by way of the Gibson assembly method (D. G. Gibson et al., *NATURE METHODS*, Vol. 6 No. 5, MAY 2009, NEBuilder HiFi DNA Assembly Master Mix), and then transformed into *E. coli* DH5a and plated on an LB solid medium containing kanamycin (25 mg/L). In order to select colonies transformed with the vector in which the desired gene and pDZTn were linked, PCR was performed using the primers of SEQ ID NOS: 47 and 48 (Table 3). Plasmids were obtained from the selected colonies using a commonly known plasmid extraction method, and the resulting plasmids were named pDZTn-Pspl13-zwf(C.gl13869) and pDZTn-Pcj7-zwf (C.gl13869).

Example 1-3. Construction of Vectors in which *Escherichia coli*-Derived Fructokinase Gene (cscK) is Enhanced The nucleotide sequence of the *Escherichia*-derived fructokinase gene has already been clearly identified and published. The cscK gene information was obtained from *Escherichia coli* W (CP002967) of NCBI, and based on the information, primers containing the polynucleotides of SEQ ID NOS: 25 and 26 (Table 7) and SEQ ID NOS: 29 and 30 (Table 8) were prepared, and PCR (Solg™ Pfu-X DNA polymerase) was performed under the conditions shown in Table 4 to thereby obtain cscK gene fragments for preparing vectors.

In order to obtain the SPL13 promoter and the CJ7 promoter, PCR (Solg™ Pfu-X DNA polymerase) was performed using the primers of SEQ ID NOS: 23 and 24 (Table 7) and SEQ ID NOS: 27 and 28 (Table 8) under the conditions of Table 4.

The amplified SPL13, CJ7 promoter regions, cscK(E.co) gene fragments, and pDZTn vector (U.S. Pat. No. 8,932,861 B2) cleaved with ScaI restriction enzyme were linked by way of the Gibson assembly method (D. G. Gibson et al., *NATURE METHODS*, Vol. 6 No. 5, MAY 2009, NEBuilder HiFi DNA Assembly Master Mix), and then transformed into *E. coli* DH5a and plated on an LB solid medium containing kanamycin (25 mg/L). In order to select colonies transformed with the vector in which the desired gene and pDZTn were linked, PCR was performed using the primers of SEQ ID NOS: 47 and 48 (Table 3). Plasmids were obtained from the selected colonies using a commonly known plasmid extraction method, and the resulting plasmids were named pDZTn-Pspl13-cscK(E.co) and pDZTn-Pcj7-cscK(E.co).

TABLE 7

| Primer Sequences of pDZTn-Pspl13-cscK(E.co) | | |
|---|---|---|
| No. | Name | DNA Sequences |
| SEQ ID NO: 23 | primer 17 | GCAGAAGGAATGAGTTCCTCGGC GCTTCATGTCAACAATC |
| SEQ ID NO: 24 | primer 18 | tgttttgatctcctccaataatc |
| SEQ ID NO: 25 | primer 19 | tattggaggagatcaaaacaATG TCAGCCAAAGTA |
| SEQ ID NO: 26 | primer 20 | GTTATTAGATGTCGGGCCCACTA TTCCAGTTCTTGTCGAC |

TABLE 8

| Primer Sequences of pDZTn-Pcj7-cscK(E.co) | | |
|---|---|---|
| No. | Name | DNA Sequences |
| SEQ ID NO: 27 | primer 21 | GCAGAAGGAATGAGTTCCTCaga aacatcccagcgctact |
| SEQ ID NO: 28 | primer 22 | gagtgtttcctttcgttgggtac |
| SEQ ID NO: 29 | primer 23 | cccaacgaaaggaaacactcATG TCAGCCAAAGTATGGGT |
| SEQ ID NO: 30 | primer 24 | GTTATTAGATGTCGGGCCCACTA TTCCAGTTCTTGTCGAC |

Example 1-4. Construction of Vectors in which *Corynebacterium glutamicum* ATCC13032-Derived Zwf and *Escherichia coli*-Derived cscK are Enhanced Vectors were prepared to confirm the simultaneous enhancing effect of the two genes by confirming the enhancing effect of the individual genes Example 1-1 and Example 1-3.

Pspl13-zwf(C.gl13032) and Pcj7-cscK(E.co) were obtained based on the pDZTn-Pspl13-zwf(C.gl13032) of Example 1-1 and pDZTn-Pcj7-cscK(E.co) of Example 1-3 as templates, respectively, by preparing primers containing the polynucleotides of SEQ ID NOS: 31 and 32 and SEQ ID NOS: 33 and 34 (Table 9) and performing PCR (Solg™ Pfu-X DNA polymerase) under the conditions of Table 4. The amplified Pspl13-zwf(C.gl13032) and Pcj7-cscK(E.co)

gene fragments and pDZTn vector (U.S. Pat. No. 8,932,861 B2) cleaved with ScaI restriction enzyme were linked by way of the Gibson assembly method (D. G. Gibson et al., *NATURE METHODS*, Vol. 6 No. 5, MAY 2009, NEBuilder HiFi DNA Assembly Master Mix), and then transformed into *E. coli* DH5a and plated on an LB solid medium containing kanamycin (25 mg/L). In order to select colonies transformed with the vector in which the desired gene and pDZTn were linked, PCR was performed using the primers of SEQ ID NOS: 47 and 48 (Table 3). A plasmid was obtained from the selected colonies using a commonly known plasmid extraction method, and the resulting plasmid was named pDZTn-Pspl13-zwf(C.gl13032)_Pcj7-cscK (E.co).

Pcj7-zwf(C.gl13032) and Pspl13-cscK(E.co) were obtained based on the pDZTn-Pcj7-zwf(C.gl13032) of Example 1-1 and pDZTn-Pspl13-cscK(E.co) of Example 1-3 as templates, respectively, by preparing primers containing the polynucleotides of SEQ ID NOS: 35 and 36 and SEQ ID NOS: 37 and 38 (Table 10) and performing PCR (Solg™ Pfu-X DNA polymerase) under the conditions of Table 4, in the same manner as above. The amplified Pcj7-zwf(C.gl13032) and Pspl13-cscK(E.co) gene fragments and pDZTn vector (U.S. Pat. No. 8,932,861 B2) cleaved with ScaI restriction enzyme were linked by way of the Gibson assembly method (D. G. Gibson et al., *NATURE METHODS*, Vol. 6 No. 5, MAY 2009, NEBuilder HiFi DNA Assembly Master Mix), and then transformed into *E. coli* DH5a and plated on an LB solid medium containing kanamycin (25 mg/L). In order to select colonies transformed with the vector in which the desired gene and pDZTn were linked, PCR was performed using the primers of SEQ ID NOS: 47 and 48 (Table 3). A plasmid was obtained from the selected colonies using a commonly known plasmid extraction method, and the resulting plasmid was named pDZTn-Pcj7-zwf(C.gl13032)_Pspl13-cscK(E.co).

TABLE 9

| Primer Sequences of pDZTn-Pspl13-zwf(C.gl13032)_Pcj7-cscK(E.co) | | |
|---|---|---|
| No. | Name | DNA Sequences |
| SEQ ID NO: 31 | primer 25 | GCAGAAGGAATGAGTTCCTCGGCGCTT CATGTCAACAATC |
| SEQ ID NO: 32 | primer 26 | ggatgtttctTTATGGCCTGCGCCA |
| SEQ ID NO: 33 | primer 27 | CAGGCCATAAagaaacatcccagcg |
| SEQ ID NO: 34 | primer 28 | GTTATTAGATGTCGGGCCCACTATTCC AGTTCTTGTCGAC |

TABLE 10

| Primer Sequences of pDZTn-Pcj7-zwf(C.gl13032)_Pspl13-cscK(E.co) | | |
|---|---|---|
| No. | Name | DNA Sequences |
| SEQ ID NO: 35 | primer 29 | GCAGAAGGAATGAGTTCCTCagaaaca tcccagcgctact |
| SEQ ID NO: 36 | primer 30 | atgaagcgccTTATGGCCTGCGCCA |
| SEQ ID NO: 37 | primer 31 | CAGGCCATAAggcgcttcatgtcaa |
| SEQ ID NO: 38 | primer 32 | GTTATTAGATGTCGGGCCCACTATTCC AGTTCTTGTCGAC |

Example 1-5. Construction of Vectors in which *Corynebacterium glutamicum* ATCC13869-Derived Zwf Derived and *Escherichia coli*-Derived cscK are Enhanced Vectors were prepared to confirm the simultaneous enhancing effect of the two genes by confirming the enhancing effect of the individual genes of Example 1-2 and Example 1-3.

Pspl13-zwf(C.gl13869) and Pcj7-cscK(E.co) were obtained based on the pDZTn-Pspl13-zwf(C.gl13869) of Example 1-2 and pDZTn-Pcj7-cscK(E.co) of Example 1-3 as templates, respectively, by preparing primers containing the polynucleotides of SEQ ID NOS: 39 and 40 and SEQ ID NOS: 41 and 42 (Table 11) and performing PCR (Solg™ Pfu-X DNA polymerase) under the conditions of Table 4. The amplified Pspl13-zwf(C.gl13869) and Pcj7-cscK(E.co) gene fragments and pDZTn vector (U.S. Pat. No. 8,932,861 B2) cleaved with ScaI restriction enzyme were linked by way of the Gibson assembly method (D. G. Gibson et al., *NATURE METHODS*, Vol. 6 No. 5, MAY 2009, NEBuilder HiFi DNA Assembly Master Mix), and then transformed into *E. coli* DH5a and plated on an LB solid medium containing kanamycin (25 mg/L). In order to select colonies transformed with the vector in which the desired gene and pDZTn were linked, PCR was performed using the primers of SEQ ID NOS: 49 and 50 (Table 3). A plasmid was obtained from the selected colonies using a commonly known plasmid extraction method, and the resulting plasmid was named pDZTn-Pspl13-zwf(C.gl13869)_Pcj7-cscK (E.co).

Pcj7-zwf(C.gl13869) and Pspl13-cscK(E.co) were obtained based on the pDZTn-Pcj7-zwf(C.gl13869) of Example 1-2 and pDZTn-Pspl13-cscK(E.co) of Example 1-3 as templates, respectively, by preparing primers containing the polynucleotides of SEQ ID NOS: 43 and 44 and SEQ ID NOS: 45 and 46 (Table 12) and performing PCR (Solg™ Pfu-X DNA polymerase) under the conditions of Table 4, in the same manner as above. The amplified Pcj7-zwf(C.gl13869) and Pspl13-cscK(E.co) gene fragments and pDZTn vector (U.S. Pat. No. 8,932,861 B2) cleaved with ScaI restriction enzyme were linked by way of the Gibson assembly method (D. G. Gibson et al., *NATURE METHODS*, Vol. 6 No. 5, MAY 2009, NEBuilder HiFi DNA Assembly Master Mix), and then transformed into *E. coli* DH5a and plated on an LB solid medium containing kanamycin (25 mg/L). In order to select colonies transformed with the vector in which the desired gene and pDZTn were linked, PCR was performed using the primers of SEQ ID NOS: 47 and 48 (Table 3). A plasmid was obtained from the selected colonies using a commonly known plasmid extraction method, and the resulting plasmid was named pDZTn-Pcj7-zwf(C.gl13869)_Pspl13-cscK(E.co).

TABLE 11

Primer Sequences of
pDZTn-Pspl13-zwf(C.gl13869)_Pcj7-cscK(E.co)

| No. | Name | DNA Sequences |
|---|---|---|
| SEQ ID NO: 39 | primer 33 | GCAGAAGGAATGAGTTCCTCGGCGCT TCATGTCAACAATC |
| SEQ ID NO: 40 | primer 34 | ggatgtttctTTATGGCCTGCGCCA |
| SEQ ID NO: 41 | primer 35 | CAGGCCATAAgaaacatcccagcg |

TABLE 11-continued

Primer Sequences of
pDZTn-Pspl13-zwf(C.gl13869)_Pcj7-cscK(E.co)

| No. | Name | DNA Sequences |
|---|---|---|
| SEQ ID NO: 42 | primer 36 | GTTATTAGATGTCGGGCCCACTATTC CAGTTCTTGTCGAC |

TABLE 12

Primer Sequences of
pDZTn-Pcj7-zwf(C.gl13869)_Pspl13-cscK(E.co)

| No. | Name | DNA Sequences |
|---|---|---|
| SEQ ID NO: 43 | primer 37 | GCAGAAGGAATGAGTTCCTCagaaaca tcccagcgctact |
| SEQ ID NO: 44 | primer 38 | atgaagcgccTTATGGCCTGCGCCA |
| SEQ ID NO: 45 | primer 39 | CAGGCCATAAggcgcttcatgtcaa |
| SEQ ID NO: 46 | primer 40 | GTTATTAGATGTCGGGCCCACTATTCC AGTTCTTGTCGAC |

Example 2. Construction of Enhanced Strains

Example 2-1. Construction of Lysine-Producing Strains in which *Corynebacterium glutamicum* ATCC13032-Derived Zwf is Enhanced The L-lysine-producing *Corynebacterium glutamicum* KCCM11016P (Korean Patent No. 10-0159812), KCCM10770P (Korean Patent No. 10-0924065), and CJ3P (Binder et al. *Genome Biology* 2012, 13:R40) strains were each transformed with the pDZTn-Pspl13-zwf(C.gl13032) and pDZTn-Pcj7-zwf(C.gl13032) vectors prepared in Example 1-1 by electroporation (Appl. Microbiol. Biotechnol. (1999) 52:541-545) and subjected to secondary crossover to thereby obtain strains in which Pspl13-zwf (C.gl13032) and Pcj7-zwf(C.gl13032) were each inserted between the transposon genes. The gene manipulation was confirmed through genome sequencing and PCR using the primers of SEQ ID NO: 47 and SEQ ID NO: 48 (Table 3), which can amplify the adjacent regions including the position at which the genes were inserted. The thus-obtained strains were named *Corynebacterium glutamicum* KCCM11016P_Pspl13-zwf(C.gl13032), KCCM11016P_Pcj7-zwf(C.gl13032), KCCM10770P_Pspl13-zwf(C.gl13032), KCCM10770P_Pcj7-zwf(C.gl13032), CJ3P_Pspl13-zwf (C.gl13032), and CJ3P_Pcj7-zwf(C.gl13032).

Example 2-2. Construction of Tryptophan-Producing Strains in which *Corynebacterium glutamicum* ATCC13869-Derived Zwf is Enhanced The L-tryptophan-producing *Corynebacterium glutamicum* KCCM12218P (Korean Patent No. 10-2035844) strain was each transformed with the pDZTn-Pspl13-zwf (C.gl13869) and pDZTn-Pcj7-zwf(C.gl13869) vectors prepared in Example 1-2 by electroporation (Appl. Microbiol. Biotechnol. (1999) 52:541-545) and subjected to secondary crossover to thereby obtain strains in which Pspl13-zwf (C.gl13869) and Pcj7-zwf(C.gl13869) were each inserted between the transposon genes. The gene manipulation was confirmed through genome sequencing and PCR using the primers of SEQ ID NO: 47 and SEQ ID NO: 48 (Table 3), which can amplify the adjacent regions including the position at which the genes were inserted. The thus-obtained strains were named *Corynebacterium glutamicum* KCCM12218P_Pspl13-zwf(C.gl13869) and KCCM12218P_Pcj7-zwf(C.gl13869).

Example 2-3. Construction of Lysine and Tryptophan-Producing Strains in which *Escherichia coli*-Derived cscK is Enhanced The L-lysine-producing *Corynebacterium glutamicum* KCCM11016P (Korean Patent No. 10-0159812), KCCM10770P (Korean Patent No. 10-0924065), and CJ3P (Binder et al. *Genome Biology* 2012, 13:R40) strains, and the L-tryptophan-producing *Corynebacterium glutamicum* KCCM12218P strain (Korean Patent No. 10-2035844) were each transformed with the pDZTn-Pspl13-cscK(E.co) and pDZTn-Pcj7-cscK(E.co) vectors prepared in Example 1-3 by electroporation (Appl. Microbiol. Biotechnol. (1999) 52:541-545) and subjected to secondary crossover to thereby obtain strains in which Pspl13-cscK(E.co) and Pcj7-cscK (E.co) were each inserted between the transposon genes. The gene manipulation was confirmed through genome sequencing and PCR using the primers of SEQ ID NO: 47 and SEQ ID NO: 48 (Table 3), which can amplify the adjacent regions including the position at which the genes were inserted. The thus-obtained lysine-producing strains were named *Corynebacterium glutamicum* KCCM11016P_Pspl13-cscK(E.co), KCCM11016P_Pcj7-cscK(E.co), KCCM10770P_Pspl13-cscK(E.co), KCCM10770P_Pcj7-cscK(E.co), CJ3P_Pspl13-cscK(E.co), and CJ3P_Pcj7-cscK(E.co), and the thus-obtained tryptophan-producing strains were named KCCM12218P_Pspl13-cscK(E.co) and KCCM12218P_Pcj7-cscK(E.co).

Example 2-4. Construction of Lysing-Producing Strains in which *Corynebacterium glutamicum* ATCC13032-Derived Zwf and *Escherichia coli*-Derived cscK are Enhanced The L-lysine-producing *Corynebacterium glutamicum* KCCM11016P (Korean Patent No. 10-0159812), KCCM10770P (Korean Patent No. 10-0924065), and CJ3P (Binder et al. *Genome Biology* 2012, 13:R40) strains were each transformed with the pDZTn-Pspl13-zwf(C. gl13032)_Pcj7-cscK(E.co) and pDZTn-Pcj7-zwf (C.gl13032)_Pspl13-cscK(E.co) vectors prepared in Example 1-4 by electroporation (*Appl. Microbiol. Biotechnol.* (1999) 52:541-545) and subjected to secondary crossover to thereby obtain strains in which Pspl13-zwf (C.gl13032)_Pcj7-cscK(E.co) and Pcj7-zwf(C.gl13032)_Pspl13-cscK(E.co) were each inserted between the transposon genes. The gene manipulation was confirmed through genome sequencing and PCR using the primers of SEQ ID NO: 47 and SEQ ID NO: 48 (Table 3), which can amplify the adjacent regions including the position at which the genes were inserted. The thus-obtained strains were named *Corynebacterium glutamicum* KCCM11016P_Pspl13-zwf (C.gl13032)_Pcj7-cscK(E.co), KCCM11016P_Pcj7-zwf (C.gl13032)_Pspl13-cscK(E.co), KCCM10770P_Pspl13-zwf(C.gl13032)_Pcj7-cscK(E.co), KCCM10770P_Pcj7-zwf (C.gl13032)_Pspl13-cscK(E.co), CJ3P_Pspl13-zwf (C.gl13032)_Pcj7-cscK(E.co), and CJ3P_Pcj7-zwf (C.gl13032)_Pspl13-cscK(E.co).

Example 2-5. Construction of Tryptophan-Producing Strains in which *Corynebacterium glutamicum* ATCC13869-Derived Zwf and *Escherichia coli*-Derived cscK are Enhanced The L-tryptophan-producing *Corynebacterium glutamicum* KCCM12218P (Korean Patent No. 10-2035844) strain was each transformed with the pDZTn-Pspl13-zwf (C.gl13869)_Pcj7-cscK(E.co) and pDZTn-Pcj7-zwf (C.gl13869)_Pspl13-cscK(E.co) vectors prepared in Example 1-5 by electroporation (Appl. Microbiol. Biotechnol. (1999) 52:541-545) and subjected to secondary crossover to thereby obtain strains in which Pspl13-zwf (C.gl13869)_Pcj7-cscK(E.co) and Pcj7-zwf(C. gl13869)_Pspl13-cscK(E.co) were each inserted between the transposon genes. The gene manipulation was confirmed through genome sequencing and PCR using the primers of SEQ ID NO: 47 and SEQ ID NO: 48 (Table 3), which can amplify the adjacent regions including the position at which the genes were inserted. The thus-obtained tryptophan-producing strains named *Corynebacterium glutamicum* KCCM12218P_Pspl13-zwf(C.gl13869)_Pcj7-cscK(E.co) and KCCM12218P_Pcj7-zwf(C.gl13869)_Pspl13-cscK (E.co).

Example 3. Comparison of L-Lysine or L-Tryptophan Producing Ability of Zwf, cscK-Enhanced Strains

Example 3-1. Comparison of L-Lysine Producing Ability of *Corynebacterium glutamicum* ATCC13032-Derived Zwf and *Escherichia coli*-Derived cscK-Enhanced Strains The KCCM11016P, KCCM10770P, and CJ3P-based strains, in which zwf(C.gl13032) and cscK(E.co) are simultaneously enhanced, prepared in Example 2-4, the KCCM11016P, KCCM10770P, and CJ3P-based zwf (C.gl13032)-enhanced strains prepared in Example 2-1, and the KCCM11016P, KCCM10770P, and CJ3P-based cscK (E.co)-enhanced strains prepared in Example 2-3 were each cultured in the following manner to compare cell mass, sugar consumption ability, and lysine producing ability.

First, each strain was seeded into a 250 mL corner-baffle flask containing 25 mL of a seed medium and cultured at 30° C. for 20 hours at 200 rpm with shaking. Then, 1 mL of the seed culture solution was seeded into a 250 mL corner-baffle flask containing 24 mL of a production medium, and cultured at 37° C. for 42 hours at 200 rpm with shaking. After completion of the culture, the production of L-lysine was measured by HPLC. The experiment was repeated 3 times, and the culture results (average values) are shown in Tables 13, 14, and 15.

<Seed Medium (pH 7.0)>

Raw sugar 20 g, Peptone 10 g, Yeast Extract 5 g, Urea 1.5 g, $KH_2PO_4$ 4 g, $K_2HPO_4$ 8 g, $MgSO_4 \cdot 7H_2O$ 0.5 g, Biotin 0.1 mg, Thiamine-HCl 1 mg, Calcium Pantothenate 22 mg, Nicotinamide 2 mg (based on 1 L of distilled water)

<Production Medium (pH 7.0)>

Raw sugar 45 g, $(NH_4)_2SO_4$ 15 g, Soybean Protein 10 g, Molasses 10 g, $KH_2PO_4$ 0.55 g, $MgSO_4 \cdot 7H_2O$ 0.6 g, Biotin 0.9 mg, Thiamine-HCl 4.5 mg, Calcium Pantothenate 4.5 mg, Nicotinamide 30 mg, MnSO$_4$ 9 mg, FeSO$_4$ 9 mg, ZnSO$_4$ 0.45 mg, CuSO$_4$ 0.45 mg, CaCO$_3$ 30 g (based on 1 L of distilled water)

It was confirmed that the above-prepared Lysine-producing strains in which zwf(C.gl13032) and cscK(E.co) were simultaneously enhanced showed the effect of improving the yield by 13.0% to 15.2% compared to the parent strain KCCM11016P, as shown in Table 13 below. By simultaneously enhancing cscK and zwf, the effect of improving the lysine yield was confirmed to be significantly increased compared to the individual enhancement by evaluating the KCCM11016P_Pspl13-zwf(C.gl13032) Pcj7-cscK(E.co) strain.

As shown in Tables 14 and 15, the same enhancement effect of the genes was observed in other lysine-producing strains of KCCM10770P and CJ3P. When both zwf (C.gl13032) and cscK(E.co) were simultaneously enhanced compared to the individually enhanced strains, the improved production results of 1.9 g/L and 1.6 g/L, which were increased by 22.1% and 27.1%, respectively, were observed compared to the parent strain.

Example 3-2. Comparison of L-Tryptophan Producing Ability of *Corynebacterium glutamicum* ATCC13869-Derived Zwf and *Escherichia coli*-Derived cscK-Enhanced Strains The KCCM12218P-based strains, in which zwf (C.gl13869) and cscK(E.co) were simultaneously enhanced, prepared in Example 2-5, the KCCM12218P-based zwf (C.gl13869)-enhanced strains prepared in Example 2-2, and the KCCM12218P-based cscK(E.co)-enhanced strains prepared in Example 2-3 were each cultured in the following manner to compare cell mass, sugar consumption ability, and tryptophan producing ability.

First, each strain was seeded into a 250 mL corner-baffle flask containing 25 mL of a seed medium and cultured at 30° C. for 20 hours at 200 rpm with shaking. Then, 1 mL of the seed culture solution was seeded into a 250 mL corner-baffle flask containing 24 mL of a production medium, and cultured at 37° C. for 42 hours at 200 rpm with shaking. After completion of the culture, the production of L-tryptophan

TABLE 13

Comparison of L-Lysine Producing Ability (Based on KCCM11016P)

| Strain | OD$_{562}$ | Sugar Consumption (g/L) | Lysine Production (g/L) | Relative to Parent Strain (%) |
|---|---|---|---|---|
| KCCM11016P | 45.6 | 50 | 13.8 | 100 |
| KCCM11016P_Pspl13-zwf(C.gl13032) | 46.1 | 50 | 14.7 | 106.5 |
| KCCM11016P_Pcj7-zwf(C.gl13032) | 46.7 | 50 | 14.5 | 105.1 |
| KCCM11016P_Pspl13-cscK(E.co) | 45.8 | 50 | 14.4 | 104.3 |
| KCCM11016P_Pcj7-cscK(E.co) | 46.4 | 50 | 14.4 | 104.3 |
| KCCM11016P_Pspl13-zwf(C.gl13032)_Pcj7-cscK(E.co) | 46.3 | 50 | 15.9 | 115.2 |
| KCCM11016P_Pcj7-zwf(C.gl13032)_Pspl13-cscK(E.co) | 45.9 | 50 | 15.6 | 113.0 |

TABLE 14

Comparison of L-Lysine Producing Ability (Based on KCCM10770P)

| Strains | OD$_{562}$ | Sugar Consumption (g/L) | Lysine Production (g/L) | Relative to Parent Strain (%) |
|---|---|---|---|---|
| KCCM10770P | 63.3 | 50 | 8.6 | 100% |
| KCCM10770P_Pspl13-zwf(C.gl13032) | 60.1 | 50 | 9.2 | 107.0% |
| KCCM10770P_Pcj7-zwf(C.gl13032) | 61.5 | 50 | 9 | 104.7% |
| KCCM10770P_Pspl13-cscK(E.co) | 65.5 | 50 | 9.1 | 105.8% |
| KCCM10770P_Pcj7-cscK(E.co) | 66.1 | 50 | 9.4 | 109.3% |
| KCCM10770P_Pspl13-zwf(C.gl13032)_Pcj7-cscK(E.co) | 64.9 | 50 | 10.5 | 122.1% |
| KCCM10770P_Pcj7-zwf(C.gl13032)Pspl13-cscK(E.co) | 64.1 | 50 | 10.2 | 118.6% |

TABLE 15

Comparison of L-Lysine Producing Ability (Based on CJ3P)

| Strain | OD$_{562}$ | Sugar Consumption (g/L) | Lysine Production (g/L) | Relative to Parent Strain (%) |
|---|---|---|---|---|
| CJ3P | 48.8 | 50 | 5.9 | 100% |
| CJ3P_Pspl13-zwf(C.gl13032) | 46.7 | 50 | 6.4 | 108.5% |
| CJ3P_Pcj7-zwf(C.gl13032) | 46.5 | 50 | 6.3 | 106.8% |
| CJ3P_Pspl13-cscK(E.co) | 50.1 | 50 | 6.1 | 103.4% |
| CJ3P_Pcj7-cscK(E.co) | 48.6 | 50 | 6.6 | 111.9% |
| CJ3P_Pspl13-zwf(C.gl13032)_Pcj7-cscK(E.co) | 49.4 | 50 | 7.5 | 127.1% |
| CJ3P_Pcj7_zwf(C.gl13032)_Pspl13-cscK(E.co) | 50.3 | 50 | 7.2 | 122.0% | was measured by HPLC. The experiment was repeated 3 times, and the culture results (average values) are shown in Table 16.

<Seed Medium (pH 7.0)>

Raw sugar 20 g, Peptone 10 g, Yeast Extract 5 g, Urea 1.5 g, KH₂PO₄ 4 g, K₂HPO₄ 8 g, MgSO₄·7H₂O 0.5 g, Biotin 100 µg, Thiamine-HCl 1000 µg, Calcium Pantothenate 2000 µg, Nicotinamide 2000 µg (based on 1 L of distilled water)

<Production Medium (pH 7.0)>

Raw sugar 30 g, (NH₄)₂SO₄ 15 g, MgSO₄·7H₂O 1.2 g, KH₂PO₄ 1 g, Yeast Extract 5 g, Biotin 900 µg, Thiamine- HCl 4500 µg, Calcium Pantothenate 4500 µg, CaCO₃ 30 g (based on 1 L of distilled water)

The above-prepared tryptophan-producing strains, in which the zwf(C.gl13869) and cscK(E.co) genes were simultaneously enhanced, showed an increase in tryptophan yield by 34.4% to 45.1% as compared to the parent strain KCCM12218P, as shown in Table 16, thereby confirming that the tryptophan yield was significantly improved as compared to the case where the two genes were individually enhanced.

TABLE 16

Comparison of L-Tryptophan Producing Ability (Based on KCCM12218P)

| Strain | OD$_{562}$ | Sugar Consumption (g/L) | Tryptophan Production (g/L) | Relative to Parent Strain (%) |
|---|---|---|---|---|
| KCCM12218P | 69.7 | 30 | 2.15 | 100 |
| KCCM12218P_Pspl13-zwf(C.gl13869) | 64.1 | 30 | 2.33 | 108.4 |
| KCCM12218P_Pcj7-zwf(C.gl13869) | 68.5 | 30 | 2.32 | 107.9 |
| KCCM12218P_Pspl13-cscK(E.co) | 61.9 | 30 | 2.65 | 123.3 |
| KCCM12218P_Pcj7-cscK(E.co) | 62.1 | 30 | 2.44 | 113.5 |
| KCCM12218P_Pspl13_zwf(C.gl13869)_Pcj7-cscK(E.co) | 61.1 | 30 | 2.89 | 134.4 |
| KCCM12218P_Pcj7_zwf(C.gl13869)_Pspl13-cscK(E.co) | 59.8 | 30 | 3.12 | 145.1 |

From the foregoing, a skilled person in the art to which the present disclosure pertains will be able to understand that the present disclosure may be embodied in other specific forms without modifying the technical concepts or essential characteristics of the present disclosure. In this regard, the exemplary embodiments disclosed herein are only for illustrative purposes and should not be construed as limiting the scope of the present disclosure. The scope of the present disclosure is therefore indicated by the appended claims rather than by the foregoing description. All changes which come within the meaning and range of equivalency of the claims are to be embraced within the scope of the present disclosure.

The invention claimed is:

1. A microorganism producing L-amino acid, in which the activity of glucose-6-phosphate 1-dehydrogenase and fructokinase is enhanced.

2. The microorganism of claim 1, wherein the glucose-6-phosphate 1-dehydrogenase comprises an amino acid sequence comprising a sequence identity of at least 80% to SEQ ID NO: 1 or SEQ ID NO: 3.

3. The microorganism of claim 1, wherein the fructokinase comprises an amino acid sequence comprising a sequence identity of at least 80% to SEQ ID NO: 5.

4. The microorganism of claim 1, wherein the L-amino acid is L-lysine or L-tryptophan.

5. A method for producing L-amino acid, comprising: culturing the microorganism of claim 1 in a medium; and recovering the L-amino acid from the microorganism or medium.

6. The method of claim 5, wherein the L-amino acid is L-lysine or L-tryptophan.

7. A composition for producing L-amino acid, comprising the microorganism of claim 1 or a culture of the microorganism.

8. The microorganism of claim 1, wherein the microorganism is genus of *Corynebacterium.*

9. The microorganism of claim 8, wherein the genus of *Corynebacterium* is *Corynebacterium glutamicum.*

10. The microorganism of claim 5, wherein the microorganism is genus of *Corynebacterium.*

11. The microorganism of claim 10, wherein the genus of *Corynebacterium* is *Corynebacterium glutamicum.*

* * * * *

```
                         SEQUENCE LISTING

Sequence total quantity: 48
SEQ ID NO: 1            moltype = AA   length = 484
FEATURE                Location/Qualifiers
REGION                 1..484
                       note = zwf (C.gl 13032)
source                 1..484
                       mol_type = protein
                       organism = synthetic construct
SEQUENCE: 1
MVIFGVTGDL ARKKLLPAIY DLANRGLLPP GFSLVGYGRR EWSKEDFEKY VRDAASAGAR  60
TEFRENVWER LAEGMEFVRG NFDDDAAFDN LAATLKRIDK TRGTAGNWAY YLSIPPDSFT  120
AVCHQLERSG MAESTEEAWR RVIIEKPFGH NLESAHELNQ LVNAVFPESS VFRIDHYLGK  180
ETVQNILALR FANQLFEPLW NSNYVDHVQI TMAEDIGLGG RAGYYDGIGA ARDVIQNHLI  240
QLLALVAMEE PISFVPAQLQ AEKIKVLSAT KPCYPLDKTS ARGQYAAGWQ GSELVKGLRE  300
EDGFNPESTT ETFAACTLEI TSRRWAGVPF YLRTGKRLGR RVTEIAVVFK DAPHQPFDGD  360
MTVSLGQNAI VIRVQPDEGV LIRFGSKVPG SAMEVRDVNM DFSYSESFTE ESPEAYERLI  420
LDALLDESSL FPTNEEVELS WKILDPILEA WDADGEPEDY PAGTWGPKSA DEMLSRNGHT  480
WRRP                                                              484

SEQ ID NO: 2            moltype = DNA   length = 1545
FEATURE                Location/Qualifiers
misc_feature           1..1545
                       note = zwf (C.gl 13032)
source                 1..1545
                       mol_type = other DNA
                       organism = synthetic construct
SEQUENCE: 2
gtgagcacaa acacgacccc ctccagctgg acaaacccac tgcgcgaccc gcaggataaa  60
```

```
cgactcccc gcatcgctgg cccttccggc atggtgatct tcggtgtcac tggcgacttg  120
gctcgaaaga agctgctccc cgccatttat gatctagcaa accgcggatt gctgcccca   180
ggattctcgt tggtaggtta cggccgccgc gaatggtcca agaagactt tgaaaaatac    240
gtacgcgatg ccgcaagtgc tggtgctcgt acggaattcc gtgaaaatgt ttgggagcgc   300
ctcgccgagg gtatggaatt tgttcgcggc aactttgatg atgatgcagc tttcgacaac   360
ctcgctgcaa cactcaagcg catcgacaaa acccgcggca ccgccggcaa ctgggcttac   420
tacctgtcca ttccaccaga ttccttcaca gcggtctgcc accagctgga gcgttccggc   480
atggctgaat ccaccgaaga agcatggcgc cgcgtgatca tcgagaagcc tttcggccac   540
aacctcgaat ccgcacacga gctcaaccag ctggtcaacg cagtcttccc agaatcttct   600
gtgttccgca tcgaccacta tttgggcaag gaaacagttc aaaacatcct ggctctgcgt   660
tttgctaacc agctgtttga gccactgtgg aactccaact acgttgacca cgtccagatc   720
accatggctg aagatattgg cttgggtgga cgtgctggtt actacgacgg catcggcgca   780
gcccgcgacg tcatccagaa ccacctgatc cagctcttgg ctctggttgc catggaagaa   840
ccaatttctt tcgtgccagc gcagctgcag gcagaaaaga tcaaggtgct ctctgcgaca   900
aagccgtgct acccattgga taaaaacctcc gctcgtggtc agtacgctgc cggttggcag   960
ggctctgagt tagtcaaggg acttcgcgaa gaagatggct tcaaccctga gtccaccact   1020
gagacttttg cggcttgtac cttagagatc acgtctcgtc gctgggctgg tgtgccgttc   1080
tacctgcgca ccggtaagcg tcttggtcgc cgtgttactg agattgccgt ggtgtttaaa   1140
gacgcaccac accagccttt cgacggcgac atgactgtat cccttggcca aaacgccatc   1200
gtgattcgcg tgcagcctga tgaaggtgtg ctcatccgct tcggttccaa ggttccaggt   1260
tctgccatgg aagtccgtga cgtcaacatg gacttctcct actcagaatc cttcactgaa   1320
gaatcacctg aagcatacga gcgcctcatt ttggatgcgc tgttagatga atccagcctc   1380
ttccctacca acgaggaagt ggaactgagc tggaagattc tggatccaat tcttgaagca   1440
tgggatgccg atggagaacc agaggattac ccagcgggta cgtgggggtcc aaagagcgct   1500
gatgaaatgc tttcccgcaa cggtcacacc tggcgcaggc cataa               1545
```

```
SEQ ID NO: 3            moltype = AA   length = 514
FEATURE                 Location/Qualifiers
REGION                  1..514
                        note = zwf(C.gl 13869)
source                  1..514
                        mol_type = protein
                        organism = synthetic construct
SEQUENCE: 3
MSTNTTPTSW TNPLRDPQDK RLPRIAGPSG MVIFGVTGDL ARKKLLPAIY DLANRGLLPP  60
GFSLVGYGRR EWSKEDFEKY VRDAASAGAR TEFRENVWER LAEGMEFVRG NFDDDAAFDN  120
LAATLKRIDK TRGTAGNWAY YLSIPPDSFT AVCHQLERSG MAESTEEAWR RVIIEKPFGH  180
NLESAHELNQ LVNAVFPESS VFRIDHYLGK ETVQNILALR FANQLFEPLW NSNYVDHVQI  240
TMAEDIGLGG RAGYYDGIGA ARDVIQNHLI QLLALVAMEE PISFVPAQLQ AEKIKVLSAT  300
KPCYPLDKTS ARGQYAAGWQ GSELVKGLRE EDGFNPESTT ETFAACTLEI TSRRWAGVPF  360
YLRTGKRLGR RVTEIAVVFK DAPHQPFDGD MTVSLGQNAI VIRVQPDEGV LIRFGSKVPG  420
SAMEVRDVNM DFSYSESFTE ESPEAYERLI LDALLDESSL FPTNEEVELS WKILDPILEA  480
WDADGEPEDY PAGTWGPKSA DEMLSRNGHT WRRP                            514
```

```
SEQ ID NO: 4            moltype = DNA   length = 1545
FEATURE                 Location/Qualifiers
misc_feature            1..1545
                        note = zwf(C.gl 13869)
source                  1..1545
                        mol_type = other DNA
                        organism = synthetic construct
SEQUENCE: 4
gtgagcacaa acacgacccc caccagctgg acaaacccac tgcgcgaccc gcaggataaa  60
cgactcccc gcatcgctgg cccttccggc atggtgatct tcggtgtcac tggcgacttg   120
gctcgaaaga agctgcttcc cgccatttat gatctagcaa accgcggatt gctgcccca    180
ggattctcgt tggtaggtta cggccgccgc gaatggtcca agaagactt tgaaaaatac    240
gtacgcgatg ccgcaagtgc tggtgctcgt acggaattcc gtgaaaatgt ttgggagcgc   300
ctcgccgagg gtatggaatt tgttcgcggc aactttgatg atgatgcagc tttcgacaac   360
ctcgctgcaa cactcaagcg catcgacaaa acccgcggca ccgccggcaa ctgggcttac   420
tacctgtcca ttccaccaga ttccttcaca gcggtctgcc accagctgga gcgttccggc   480
atggctgaat ccaccgaaga agcatggcgc cgcgtgatca tcgagaagcc tttcggccac   540
aacctcgaat ccgcacacga gctcaaccag ctggtcaacg cagtcttccc agaatcttct   600
gtgttccgca tcgaccacta tttgggcaag gaaacagttc aaaacatcct ggctctgcgt   660
tttgctaacc agctgtttga gccactgtgg aactccaact acgttgacca cgtccagatc   720
accatggctg aagatatcgg cttgggtgga cgtgctggtt actacgacgg catcggtgca   780
gcccgcgacg tcatccagaa ccacctgatc cagctcttgg ctctggttgc catggaagaa   840
ccaatttctt tcgtgccagc gcagctgcag gcagaaaaga tcaaggtgct ctctgcgaca   900
aagccatgct acccattgga taaaaacctcc gctcgtggtc agtacgctgc cggttggcag   960
ggctctgagt tagtcaaggg acttcgcgaa gaagatggct tcaaccctga gtccaccact   1020
gagacttttg cggcttgtac cttagagatc acgtctcgtc gctgggctgg tgtgccgttc   1080
tacctgcgca ccggtaagcg tcttggtcgc cgtgttactg agattgccgt ggtgtttaaa   1140
gacgcaccac accagccttt cgacggcgac atgactgtat cccttggcca aaacgccatc   1200
gtgattcgcg tgcagcctga tgaaggtgtg ctcatccgct tcggttccaa ggttccaggt   1260
tctgccatgg aagtccgtga cgtcaacatg gacttctcct actcagaatc cttcactgaa   1320
gaatcacctg aagcatacga gcgcctcatt ttggatcgc tgttggatga tccagcctc     1380
ttccccacca acgaggaagt ggaactgagc tggaagattc tggatccaat tcttgaagca   1440
tgggacgccg atggagaacc agaggattac ccagcaggta cgtgggggtcc aaagagcgct   1500
gatgaaatgc tttcccgcaa cggtcacacc tggcgcaggc cataa               1545
```

```
SEQ ID NO: 5           moltype = AA   length = 304
FEATURE                Location/Qualifiers
REGION                 1..304
                       note = cscK(E.coli)
source                 1..304
                       mol_type = protein
                       organism = synthetic construct
SEQUENCE: 5
MSAKVWVLGD AVVDLLPESD GRLLPCPGGA PANVAVGIAR LGGTSGFIGR VGDDPFGALM    60
QRTLLTEGVD ITYLKQDEWH RTSTVLVDLN DQGERSFTFM VRPSADLFLE TTDLPCWRHG   120
EWLHLCSIAL SAEPSRTSAF TAMTAIRHAG GFVSFDPNIR EDLWQDEHLL RLCLRQALQL   180
ADVVKLSEEE WRLISGKTQN DQDICALAKE YEIAMLLVTK GAEGVVVCYR GQVHHFAGMS   240
VNCVDSTGAG DAFVAGLLTG LSSTGLSTDE REMRRIIDLA QRCGALAVTA KGAMTALPCR   300
QELE                                                                304

SEQ ID NO: 6           moltype = DNA   length = 915
FEATURE                Location/Qualifiers
misc_feature           1..915
                       note = cscK(E.coli)
source                 1..915
                       mol_type = other DNA
                       organism = synthetic construct
SEQUENCE: 6
atgtcagcca aagtatgggt tttaggggat gcggtcgtag atctcttgcc agaatcagac    60
gggcgcctac tgccttgtcc tggcggcgcg ccagctaacg ttgcggtggg aatcgccaga   120
ttaggcggaa caagtgggtt tataggtcgg gtggggcatg atcctttgg tgcgttaatg    180
caaagaacgc tgctaactga gggagtcgat atcacgtatc tgaagcaaga tgaatggcac   240
cggacatcca cggtgcttgt cgatctgaac gatcaagggg aacgttcatt tacgtttatg   300
gtccgcccca gtgccgatct ttttttagag acgacagact tgccctgctg gcgacatggc   360
gaatggttac atctctgttc aattgcgttg tctgccgagc cttcgcgtac cagcgcattt   420
actgcgatga cggcgatccg gcatgccgga ggtttgtca gcttcgatcc taatattcgt    480
gaagatctat ggcaagacga gcatttgctc cgcttgtgtt tgcggcaggc gctacaactg   540
gcggatgtcg tcaagctctc ggaagaagaa tggcgactta tcagtggaaa aacacagaac   600
gatcaggata tatgcgccct ggcaaaagag tatgagatcc ccatgctgtt ggtgactaaa   660
ggtgcagaag gggtggttgg tctgttatcga ggacaagttc accattttgc tggaatgtct   720
gtgaattgtg tcgatagcac gggggcggga gatgcgttcg ttgccgggtt actcacaggt   780
ctgtcctcta cgggattatc tacagatgag agagaaatgc gacgaattat cgatctcgct   840
caacgttgcg gagcgcttgc agtaacggcg aaagggggcaa tgacagcgct gccatgtcga   900
caagaactgg aatag                                                    915

SEQ ID NO: 7           moltype = DNA   length = 40
FEATURE                Location/Qualifiers
misc_feature           1..40
                       note = primer 1
source                 1..40
                       mol_type = other DNA
                       organism = synthetic construct
SEQUENCE: 7
gcagaaggaa tgagttcctc ggcgcttcat gtcaacaatc                          40

SEQ ID NO: 8           moltype = DNA   length = 23
FEATURE                Location/Qualifiers
misc_feature           1..23
                       note = primer 2
source                 1..23
                       mol_type = other DNA
                       organism = synthetic construct
SEQUENCE: 8
tgttttgatc tcctccaata atc                                           23

SEQ ID NO: 9           moltype = DNA   length = 35
FEATURE                Location/Qualifiers
misc_feature           1..35
                       note = primer 3
source                 1..35
                       mol_type = other DNA
                       organism = synthetic construct
SEQUENCE: 9
tattggagga gatcaaaaca gtgagcacaa acacg                              35

SEQ ID NO: 10          moltype = DNA   length = 40
FEATURE                Location/Qualifiers
misc_feature           1..40
                       note = primer 4
source                 1..40
                       mol_type = other DNA
                       organism = synthetic construct
SEQUENCE: 10
gttattagat gtcgggccca ttatggcctg cgccaggtgt                          40
```

-continued

```
SEQ ID NO: 11              moltype = DNA   length = 40
FEATURE                    Location/Qualifiers
misc_feature               1..40
                           note = primer 5
source                     1..40
                           mol_type = other DNA
                           organism = synthetic construct
SEQUENCE: 11
gcagaaggaa tgagttcctc agaaacatcc cagcgctact                            40

SEQ ID NO: 12              moltype = DNA   length = 23
FEATURE                    Location/Qualifiers
misc_feature               1..23
                           note = primer 6
source                     1..23
                           mol_type = other DNA
                           organism = synthetic construct
SEQUENCE: 12
gagtgtttcc tttcgttggg tac                                              23

SEQ ID NO: 13              moltype = DNA   length = 35
FEATURE                    Location/Qualifiers
misc_feature               1..35
                           note = primer 7
source                     1..35
                           mol_type = other DNA
                           organism = synthetic construct
SEQUENCE: 13
cccaacgaaa ggaaacactc gtgagcacaa acacg                                 35

SEQ ID NO: 14              moltype = DNA   length = 40
FEATURE                    Location/Qualifiers
misc_feature               1..40
                           note = primer 8
source                     1..40
                           mol_type = other DNA
                           organism = synthetic construct
SEQUENCE: 14
gttattagat gtcgggccca ttatggcctg cgccaggtgt                            40

SEQ ID NO: 15              moltype = DNA   length = 40
FEATURE                    Location/Qualifiers
misc_feature               1..40
                           note = primer 9
source                     1..40
                           mol_type = other DNA
                           organism = synthetic construct
SEQUENCE: 15
gcagaaggaa tgagttcctc ggcgcttcat gtcaacaatc                            40

SEQ ID NO: 16              moltype = DNA   length = 23
FEATURE                    Location/Qualifiers
misc_feature               1..23
                           note = primer 10
source                     1..23
                           mol_type = other DNA
                           organism = synthetic construct
SEQUENCE: 16
tgttttgatc tcctccaata atc                                              23

SEQ ID NO: 17              moltype = DNA   length = 35
FEATURE                    Location/Qualifiers
misc_feature               1..35
                           note = primer 11
source                     1..35
                           mol_type = other DNA
                           organism = synthetic construct
SEQUENCE: 17
tattggagga gatcaaaaca gtgagcacaa acacg                                 35

SEQ ID NO: 18              moltype = DNA   length = 40
FEATURE                    Location/Qualifiers
misc_feature               1..40
                           note = primer 12
source                     1..40
                           mol_type = other DNA
                           organism = synthetic construct
SEQUENCE: 18
```

-continued
_____

```
gttattagat gtcgggccca ttatggcctg cgccaggtgt                          40

SEQ ID NO: 19           moltype = DNA   length = 40
FEATURE                 Location/Qualifiers
misc_feature            1..40
                        note = primer 13
source                  1..40
                        mol_type = other DNA
                        organism = synthetic construct
SEQUENCE: 19
gcagaaggaa tgagttcctc agaaacatcc cagcgctact                          40

SEQ ID NO: 20           moltype = DNA   length = 23
FEATURE                 Location/Qualifiers
misc_feature            1..23
                        note = primer 14
source                  1..23
                        mol_type = other DNA
                        organism = synthetic construct
SEQUENCE: 20
gagtgtttcc tttcgttggg tac                                            23

SEQ ID NO: 21           moltype = DNA   length = 35
FEATURE                 Location/Qualifiers
misc_feature            1..35
                        note = primer 15
source                  1..35
                        mol_type = other DNA
                        organism = synthetic construct
SEQUENCE: 21
cccaacgaaa ggaaacactc gtgagcacaa acacg                               35

SEQ ID NO: 22           moltype = DNA   length = 40
FEATURE                 Location/Qualifiers
misc_feature            1..40
                        note = primer 16
source                  1..40
                        mol_type = other DNA
                        organism = synthetic construct
SEQUENCE: 22
gttattagat gtcgggccca ttatggcctg cgccaggtgt                          40

SEQ ID NO: 23           moltype = DNA   length = 40
FEATURE                 Location/Qualifiers
misc_feature            1..40
                        note = primer 17
source                  1..40
                        mol_type = other DNA
                        organism = synthetic construct
SEQUENCE: 23
gcagaaggaa tgagttcctc ggcgcttcat gtcaacaatc                          40

SEQ ID NO: 24           moltype = DNA   length = 23
FEATURE                 Location/Qualifiers
misc_feature            1..23
                        note = primer 18
source                  1..23
                        mol_type = other DNA
                        organism = synthetic construct
SEQUENCE: 24
tgttttgatc tcctccaata atc                                            23

SEQ ID NO: 25           moltype = DNA   length = 35
FEATURE                 Location/Qualifiers
misc_feature            1..35
                        note = primer 19
source                  1..35
                        mol_type = other DNA
                        organism = synthetic construct
SEQUENCE: 25
tattggagga gatcaaaaca atgtcagcca aagta                               35

SEQ ID NO: 26           moltype = DNA   length = 40
FEATURE                 Location/Qualifiers
misc_feature            1..40
                        note = primer 20
source                  1..40
                        mol_type = other DNA
                        organism = synthetic construct
```

```
SEQUENCE: 26
gttattagat gtcgggccca ctattccagt tcttgtcgac                                  40

SEQ ID NO: 27          moltype = DNA   length = 40
FEATURE                Location/Qualifiers
misc_feature           1..40
                       note = primer 21
source                 1..40
                       mol_type = other DNA
                       organism = synthetic construct
SEQUENCE: 27
gcagaaggaa tgagttcctc agaaacatcc cagcgctact                                  40

SEQ ID NO: 28          moltype = DNA   length = 23
FEATURE                Location/Qualifiers
misc_feature           1..23
                       note = primer 22
source                 1..23
                       mol_type = other DNA
                       organism = synthetic construct
SEQUENCE: 28
gagtgtttcc tttcgttggg tac                                                    23

SEQ ID NO: 29          moltype = DNA   length = 40
FEATURE                Location/Qualifiers
misc_feature           1..40
                       note = primer 23
source                 1..40
                       mol_type = other DNA
                       organism = synthetic construct
SEQUENCE: 29
cccaacgaaa ggaaacactc atgtcagcca aagtatgggt                                  40

SEQ ID NO: 30          moltype = DNA   length = 40
FEATURE                Location/Qualifiers
misc_feature           1..40
                       note = primer 24
source                 1..40
                       mol_type = other DNA
                       organism = synthetic construct
SEQUENCE: 30
gttattagat gtcgggccca ctattccagt tcttgtcgac                                  40

SEQ ID NO: 31          moltype = DNA   length = 40
FEATURE                Location/Qualifiers
misc_feature           1..40
                       note = primer 25
source                 1..40
                       mol_type = other DNA
                       organism = synthetic construct
SEQUENCE: 31
gcagaaggaa tgagttcctc ggcgcttcat gtcaacaatc                                  40

SEQ ID NO: 32          moltype = DNA   length = 25
FEATURE                Location/Qualifiers
misc_feature           1..25
                       note = primer 26
source                 1..25
                       mol_type = other DNA
                       organism = synthetic construct
SEQUENCE: 32
ggatgtttct ttatggcctg cgcca                                                  25

SEQ ID NO: 33          moltype = DNA   length = 25
FEATURE                Location/Qualifiers
misc_feature           1..25
                       note = primer 27
source                 1..25
                       mol_type = other DNA
                       organism = synthetic construct
SEQUENCE: 33
caggccataa agaaacatcc cagcg                                                  25

SEQ ID NO: 34          moltype = DNA   length = 40
FEATURE                Location/Qualifiers
misc_feature           1..40
                       note = primer 28
source                 1..40
                       mol_type = other DNA
```

-continued

```
                              organism = synthetic construct
SEQUENCE: 34
gttattagat gtcgggccca ctattccagt tcttgtcgac                              40

SEQ ID NO: 35              moltype = DNA  length = 40
FEATURE                    Location/Qualifiers
misc_feature               1..40
                           note = primer 29
source                     1..40
                           mol_type = other DNA
                           organism = synthetic construct
SEQUENCE: 35
gcagaaggaa tgagttcctc agaaacatcc cagcgctact                              40

SEQ ID NO: 36              moltype = DNA  length = 25
FEATURE                    Location/Qualifiers
misc_feature               1..25
                           note = primer 30
source                     1..25
                           mol_type = other DNA
                           organism = synthetic construct
SEQUENCE: 36
atgaagcgcc ttatggcctg cgcca                                              25

SEQ ID NO: 37              moltype = DNA  length = 25
FEATURE                    Location/Qualifiers
misc_feature               1..25
                           note = primer 31
source                     1..25
                           mol_type = other DNA
                           organism = synthetic construct
SEQUENCE: 37
caggccataa ggcgcttcat gtcaa                                              25

SEQ ID NO: 38              moltype = DNA  length = 40
FEATURE                    Location/Qualifiers
misc_feature               1..40
                           note = primer 32
source                     1..40
                           mol_type = other DNA
                           organism = synthetic construct
SEQUENCE: 38
gttattagat gtcgggccca ctattccagt tcttgtcgac                              40

SEQ ID NO: 39              moltype = DNA  length = 40
FEATURE                    Location/Qualifiers
misc_feature               1..40
                           note = primer 33
source                     1..40
                           mol_type = other DNA
                           organism = synthetic construct
SEQUENCE: 39
gcagaaggaa tgagttcctc ggcgcttcat gtcaacaatc                              40

SEQ ID NO: 40              moltype = DNA  length = 25
FEATURE                    Location/Qualifiers
misc_feature               1..25
                           note = primer 34
source                     1..25
                           mol_type = other DNA
                           organism = synthetic construct
SEQUENCE: 40
ggatgtttct ttatggcctg cgcca                                              25

SEQ ID NO: 41              moltype = DNA  length = 25
FEATURE                    Location/Qualifiers
misc_feature               1..25
                           note = primer 35
source                     1..25
                           mol_type = other DNA
                           organism = synthetic construct
SEQUENCE: 41
caggccataa agaaacatcc cagcg                                              25

SEQ ID NO: 42              moltype = DNA  length = 40
FEATURE                    Location/Qualifiers
misc_feature               1..40
                           note = primer 36
source                     1..40
```

```
                              mol_type = other DNA
                              organism = synthetic construct
SEQUENCE: 42
gttattagat gtcgggccca ctattccagt tcttgtcgac                              40

SEQ ID NO: 43          moltype = DNA  length = 40
FEATURE                Location/Qualifiers
misc_feature           1..40
                       note = primer 37
source                 1..40
                       mol_type = other DNA
                       organism = synthetic construct
SEQUENCE: 43
gcagaaggaa tgagttcctc agaaacatcc cagcgctact                              40

SEQ ID NO: 44          moltype = DNA  length = 25
FEATURE                Location/Qualifiers
misc_feature           1..25
                       note = primer 38
source                 1..25
                       mol_type = other DNA
                       organism = synthetic construct
SEQUENCE: 44
atgaagcgcc ttatggcctg cgcca                                             25

SEQ ID NO: 45          moltype = DNA  length = 25
FEATURE                Location/Qualifiers
misc_feature           1..25
                       note = primer 39
source                 1..25
                       mol_type = other DNA
                       organism = synthetic construct
SEQUENCE: 45
caggccataa ggcgcttcat gtcaa                                             25

SEQ ID NO: 46          moltype = DNA  length = 40
FEATURE                Location/Qualifiers
misc_feature           1..40
                       note = primer 40
source                 1..40
                       mol_type = other DNA
                       organism = synthetic construct
SEQUENCE: 46
gttattagat gtcgggccca ctattccagt tcttgtcgac                              40

SEQ ID NO: 47          moltype = DNA  length = 20
FEATURE                Location/Qualifiers
misc_feature           1..20
                       note = primer 41
source                 1..20
                       mol_type = other DNA
                       organism = synthetic construct
SEQUENCE: 47
acgacgctgg tatttctccc                                                   20

SEQ ID NO: 48          moltype = DNA  length = 20
FEATURE                Location/Qualifiers
misc_feature           1..20
                       note = primer 42
source                 1..20
                       mol_type = other DNA
                       organism = synthetic construct
SEQUENCE: 48
tgattgtcga tatgaccggg                                                   20
```